United States Patent
Cheng et al.

(10) Patent No.: US 8,124,591 B2
(45) Date of Patent: Feb. 28, 2012

(54) DNA VACCINE COMPRISING IL-6-ENCODING DNA CONSTRUCT AND APPLICATIONS THEREOF

(75) Inventors: Wen-Fang Cheng, Taipei (TW); Chi-An Chen, Taipei (TW)

(73) Assignee: National Taiwan University, Taipei (TW)

( * ) Notice: Subject to any disclaimer, the term of this patent is extended or adjusted under 35 U.S.C. 154(b) by 346 days.

(21) Appl. No.: 12/003,805

(22) Filed: Jan. 2, 2008

(65) Prior Publication Data

US 2009/0169634 A1 Jul. 2, 2009

(51) Int. Cl.
*C12N 15/19* (2006.01)
*A01N 25/26* (2006.01)
*C07H 21/04* (2006.01)

(52) U.S. Cl. ........ 514/44; 424/421; 536/23.1; 536/23.4; 536/23.5

(58) Field of Classification Search .................. 424/421; 514/44; 536/23.1, 23.4, 23.5
See application file for complete search history.

(56) References Cited

U.S. PATENT DOCUMENTS
2007/0026076 A1* 2/2007 Wu et al. .................. 424/489

FOREIGN PATENT DOCUMENTS
WO WO 99/13092 * 3/1999

OTHER PUBLICATIONS

Kim et al, Cancer Res. 65:309-316, 2005.*
Tonouchi et al, GenBank Accession M29150.1, GI:186349, 1995.*
Alberts et al, Molecular Biology of the Cell, Third edition, Garland Publishing, New York, NY, 1994.*

* cited by examiner

*Primary Examiner* — Kevin K. Hill
(74) *Attorney, Agent, or Firm* — Wang Law Firm, Inc.; Li K. Wang (57) ABSTRACT

The present invention provides a DNA vaccine, which comprises a DNA construct comprising an expression vector which is expressible in a eukaryotic cell, and a nucleotide fragment which comprises an IL-6-encoding sequence and an HPV E7-encoding sequence. In addition, the present invention also provides a pharmaceutical composition and a method of generating said DNA vaccine.

19 Claims, 7 Drawing Sheets

```
                        SEQUENCE LISTING

<160> NUMBER OF SEQ ID NOS: 8

<210> SEQ ID NO 1
<211> LENGTH: 29
<212> TYPE: DNA
<213> ORGANISM: Artificial
<220> FEATURE:
<223> OTHER INFORMATION: primer

<400> SEQUENCE: 1
ccgctcgaga ggagcccagc tatgaactc                                       29

<210> SEQ ID NO 2
<211> LENGTH: 29
<212> TYPE: DNA
<213> ORGANISM: Artificial
<220> FEATURE:
<223> OTHER INFORMATION: primer

<400> SEQUENCE: 2
ccggaattcg accagaagaa ggaatgccc                                       29

<210> SEQ ID NO 3
<211> LENGTH: 700
<212> TYPE: DNA
<213> ORGANISM: Human

<400> SEQUENCE: 3
aggagcccag ctatgaactc cttctccaca agcgccttcg gtccagttgc cttctccctg     60
gggctgctcc tggtgttgcc tgctgccttc cctgccccag taccccagg agaagattcc     120 aaagatgtag ccgccccaca cagacagcca ctcacctctt cagaacgaat tgacaaacaa    180
```

-continued

```
attcggtaca tcctcgacgg catctcagcc ctgagaaagg agacatgtaa caagagtaac      240
atgtgtgaaa gcagcaaaga ggcactggca gaaaacaacc tgaaccttcc aaagatggct      300
gaaaaagatg gatgcttcca atctggattc aatgaggaga cttgcctggt gaaaatcatc      360
actggtcttt tggagtttga ggtataccta gagtacctcc agaacagatt tgagagtagt      420
gaggaacaag ccagagctgt gcagatgagt acaaaagtcc tgatccagtt cctgcagaaa      480
aaggcaaaga atctagatgc aataaccacc cctgacccaa ccacaaatgc agcctgctg       540 acgaagctgc aggcacagaa ccagtggctg caggacatga caactcatct cattctgcgc      600
agctttaagg agttcctgca gtccagcctg agggctcttc ggcaaatgta gcatgggcac      660
ctcagattgt tgttgttaat gggcattcct tcttctggtc                            700
```

```
<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
ccggaagctt atgcatggag atacacctac                                        30

<210> SEQ ID NO 5
<211> LENGTH: 23
<212> TYPE: DNA
<213> ORGANISM: Artificial
<220> FEATURE:
<223> OTHER INFORMATION: primer

<400> SEQUENCE: 5
cccaagcttt tgagaacaga tgg                                               23

<210> SEQ ID NO 6
<211> LENGTH: 288
<212> TYPE: DNA
<213> ORGANISM: human papillomavirus 16

<400> SEQUENCE: 6
atgcatggag atacacctac attgcatgaa tatatgttag atttgcaacc agagacaact       60
gatctctact gttatgagca attaaatgac agctcagagg aggaagatga aatagatggt      120
ccagctggac aagcagaacc ggacagagcc cattacaata ttgtaacctt tgttgcaag       180 tgtgactcta cgcttcggtt gtgcgtacaa agcacacacg tagacattcg tactttggaa      240
gacctgttaa tgggcacact aggaattgtg tgccccatct gttctcaa                   288

<210> SEQ ID NO 7
<211> LENGTH: 9
<212> TYPE: PRT
<213> ORGANISM: human papillomavirus 16

<400> SEQUENCE: 7

Arg Ala His Tyr Asn Ile Val Thr Phe
1               5

<210> SEQ ID NO 8
<211> LENGTH: 38
<212> TYPE: PRT
<213> ORGANISM: human papillomavirus 16

<400> SEQUENCE: 8

Asp Ser Ser Glu Glu Glu Asp Glu Ile Asp Gly Pro Ala Gly Gln Ala
```

```
                                        -continued
1               5                  10                 15

Glu Pro Asp Arg Ala His Tyr Asn Ile Val Thr Phe Cys Cys Lys Cys
            20                  25                 30

Asp Ser Thr Leu Arg Leu
            35
```

DNA VACCINE COMPRISING IL-6-ENCODING DNA CONSTRUCT AND APPLICATIONS THEREOF

BACKGROUND OF THE INVENTION

1. Field of the Invention

The present invention relates to a DNA vaccine comprising a DNA construct. The present invention also relates to a pharmaceutical composition and a method of generating said DNA vaccine.

2. Description of the Related Art

Cervical cancer is a main cause of death in women, and persistent infection with known high-risk Human papillomavirus (HPV) types, such as HPV subtype 16 (HPV-16) is directly linked to development and progression of cervical cancer. Although the present HPV vaccines can be used to prevent cervical cancer, it is not yet known whether they are useful for treating HPV-associated cervical cancer or ameliorating the existing HPV infection or HPV-associated lesions. Therefore, it is advantageous to develop a safe and effective therapeutic vaccine for treatment of HPV-associated cervical cancer, HPV-associated other genital cancers (e.g., vaginal, vulvar, penile) and other HPV-associated lesions of head and neck, and gastrointestinal system, as well as for the treatment of precancerous lesions of the same areas.

In recent years, DNA vaccines have been developed and evaluated in a variety of disease models as promising therapeutic agents for treating a variety of diseases including their use as immunotherapy in certain cancers. Therapeutic DNA vaccines are introduced into antigen-presenting cells (APCs) of the recipient's immune system to express a protein antigen, the protein antigen is processed and presented by the major histocompatibility antigen (MHC) class I and II molecules to induce immune responses, such as helper T-cell response, cytotoxic T-cell response and humoral (antibody) response, and a direct result is that tumor cells expressing said antigen can be eliminated by the immune system.

In comparison with "traditional" (protein antigen) vaccines, DNA vaccines have many advantages such as high specificity, safety, stability, cost-effectiveness, and the ability to induce several types of immune responses. DNA vaccines do not pose any risk of infection because only certain sequences of the pathogen's DNA is used in their manufacture, in contrast to "live" and "attenuated" vaccines. Also, no toxic adjuvants are needed for practical use of DNA vaccines. DNA vaccines are also easier to prepare than "subunit" vaccines because no protein antigens need to be expressed and purified prior to injection into the patient.

However, because the lifespan of APCs is limited, the efficacy of DNA vaccines is limited because APCs are not able to process and present the antigen indefinitely. Therefore, several strategies have been applied to increase the potency of DNA vaccines, such as targeting an antigen by fusing molecules to enhance antigen processing (Cheng et al., 2001; Chen et al., 2000), targeting antigens for rapid intracellular degradation (Rodriguez et al., 1997), directing antigens to APCs by fusion to ligands for APC receptors (Boyle et al., 1998) or to a pathogen sequence such as fragment C of tetanus toxin (King et al., 1998), co-injecting cytokines (Weiss et al., 1998), and administering with CpG oligonucleotides (Klinman et al., 1997).

Combined strategies for enhancing the effects of DNA vaccines have been introduced in the development of cancer vaccines and immunotherapy, and overexpression of an anti-apoptotic molecule is a potential strategy for overcoming the short lifespan of APCs. For example, the administration of a DNA vaccine which comprises fragments encoding an antigen and an inhibitor of apoptosis of dendritic cells (DCs) can prolong the survival of DCs, thereby enhancing the potency of the DNA vaccine (Kim et al., 2003). Other research has demonstrated that combining a tumor antigen and an apoptosis inhibitor, such as Bcl-X1, Bcl-2, XIAP, dominant negative caspase-9, or dominant negative caspase-8, can enhance the antigen-specific immunity and the anti-tumor effects (Kim et al., 2003; Kim et al., 2004; Kim et al., 2005). Thus, DC-based vaccination could be enhanced by an approach that inhibits apoptosis and prolongs the survival of antigen-expressing DCs in vivo. However, some apoptosis inhibitors, such as proteins of Bcl-2 family, are known to be over-expressed in some cancers and therefore they are implicated in contributing to cellular immortalization. This safety issue cannot be ignored.

SUMMARY OF THE INVENTION

In view of the disadvantages of conventional DNA vaccines, the objective of the present invention is to develop a DNA vaccine having an improved potency, which comprises a sequence obtained from the human interleukin-6 (IL-6) gene and a sequence obtained from E7 gene of Human Papillomaviruses. The combination of IL-6 and E7 prolongs the life of DCs, improves the processing and presentation of the E7 antigen, and enhances the recipient's immune responses.

Another objective of the present invention is to provide a pharmaceutical composition comprising said DNA vaccine and an optional pharmaceutically acceptable carrier. Yet another objective of the present invention is to provide a method of generating said DNA vaccine.

To achieve the above-mentioned objectives, the present invention provides a DNA construct, comprising:
- an expression vector, which is expressible in a eukaryotic cell; and
- a nucleotide fragment, which comprises an IL-6-encoding sequence, and an E7-encoding sequence.

Said E7-encoding sequence can be derived from all HPV subtypes, particularly, from HPV-16.

In preferred embodiments, said expression vector is expressible in human cells; more preferably, said expression vector is selected from pcDNA3, pSG5, or pCMV; and most preferably, said expression vector is pcDNA3.

In preferred embodiments, said IL-6-encoding sequence is SEQ ID NO: 3, and said E7-encoding sequence is SEQ ID NO: 6.

The present invention also provides a DNA vaccine, comprising:
- the above-mentioned DNA construct; and
- a particle, which is coated with said DNA construct.

In preferred embodiments, said particle is a gold particle; more preferably, said gold particle has a diameter of 1.6 μm.

In preferred embodiments, wherein said expression vector is expressible in human cells; more preferably, said expression vector is selected from pcDNA3, pSG5, or pCMV; and most preferably, said expression vector is pcDNA3.

In preferred embodiments, said IL-6-encoding sequence is SEQ ID NO: 3, and said E7-encoding sequence is SEQ ID NO: 6.

The present invention even provides a pharmaceutical composition, comprising the above-mentioned DNA vaccine.

In preferred embodiments, said pharmaceutical composition further comprising a pharmaceutically acceptable carrier; more preferably, said pharmaceutically acceptable carrier is ddH$_2$O or PBS (phosphate buffered saline).

In preferred embodiments, said pharmaceutical composition is used to treat HPV-induced diseases; more preferably, used to treat a genital cancer (e.g., cervical cancer, vaginal cancer, vulvar cancer, penile cancer) or a precancerous lesion (e.g., cervical, vulvar, or vaginal precancerous lesion), a head and neck cancer (e.g., oropharyngeal squamous cell carcinoma), or a gastrointestinal cancer (e.g., esophageal cancer, or colorectal cancer); most preferably, used to treat cervical cancer.

The present invention yet provides a method of generating the above-mentioned DNA vaccine, comprising:
(1) providing a DNA construct comprising:
    an expression vector, which is expressible in a eukaryotic cell; and
    a nucleotide fragment, which comprises an IL-6-encoding sequence, and an E7-encoding sequence; and
(2) coating said DNA construct on the surface of a particle.

In preferred embodiments, said expression vector is pcDNA3; said IL-6-encoding sequence is SEQ ID NO: 3, and said E7-encoding sequence is SEQ ID NO: 6; more preferably, said particle is a gold particle; and most preferably, said gold particle has a diameter of 1.6 μm.

The present invention further provides a method for preventing or treating a HPV-induced disease, comprising:
administering an effective amount of the above-mentioned DNA vaccine or an effective amount of the pharmaceutical composition according to Claim 12 to a subject having or at risk for developing said HPV-induced disease.

In preferred embodiments, said HPV-induced disease is a genital cancer or precancerous lesion, a head and neck cancer, or a gastrointestinal cancer; more preferably, said genital cancer comprises cervical cancer, vaginal cancer, vulvar cancer, and penile cancer; said genital precancerous lesion comprises cervical, vulvar, and vaginal precancerous lesions; said head and neck cancer comprises oropharyngeal squamous cell carcinoma, and said gastrointestinal cancer comprises esophageal cancer, colorectal and anal cancer and precancerous lesions of the same; most preferably, said HPV-induced disease is cervical cancer.

In summary, the present invention provides a DNA vaccine, which comprises a DNA construct comprising an expression vector which is expressible in a eukaryotic cell, and a nucleotide fragment which comprises an IL-6-encoding sequence and an E7-encoding sequence; which has an excellent potency and can be used for the treatment of HPV-induced diseases. Also, the present invention provides a pharmaceutical composition and a method of generating said DNA vaccine.

BRIEF DESCRIPTION OF THE DRAWINGS

FIG. 2 shows the results of the E7-specific immunological profiles of vaccinated mice. (a) Representative figures from the flow cytometric analysis of E7-specific IFN-γ-secreting CD4$^+$ T lymphocytes in each group. (b) Bar graph depicting the number of E7-specific IFN-γ-secreting CD4$^+$ T lymphocytes per $3.5 \times 10^5$ splenocytes (mean±SEM, P<0.05, one-way ANOVA). (c) Bar graph depicting the number of E7-specific IL-4-secreting CD4$^+$ T lymphocytes per $3.5 \times 10^5$ splenocytes (mean±SEM, P<0.01, one-way ANOVA). (d) Representative figures from the flow cytometric analysis of E7-specific IFN-γ-secreting CD8$^+$ T lymphocytes in each group. (e) Bar graph depicting the number of E7-specific IFN-γ-secreting CD8$^+$ T lymphocytes per $3.5 \times 10^5$ splenocytes (mean±SEM, P<0.01, one-way ANOVA). (f) Bar graph showing E7-specific antibodies in mice vaccinated with various DNA vaccines (mean±SEM, P<0.01, one-way ANOVA).

DETAILED DESCRIPTION OF THE PREFERRED EMBODIMENTS

HPV early genes are potentially useful as target antigens for therapeutic HPV vaccines because these early genes are expressed throughout the life cycle of HPV. The HPV early genes E6 and E7 (also known as oncogenes because of their ability to transform the host cells) are especially desirable for use in DNA vaccines to treat HPV-induced diseases, including genital, head and neck, and gastrointestinal cancers and related precancerous lesions. However, many DNA vaccines lack sufficient immunogenicity to render them useful because the DNA comprising the vaccines cannot amplify or spread in vivo, and antigen processing and presentation plays an important role in the production of useful therapeutic DNA vaccines.

Interleukin-6 (IL-6) is a cytokine expressed and secreted by normal cells, which plays an important role in the expansion and activation of T cells and in the differentiation of B cells. It also protects cells from apoptosis via the myeloid cell leukemia-1 (Mcl-1) pathway. These properties of IL-6 make it a desirable candidate for use in prolonging the lifespan of APCs, thereby improving the immune responses elicited by DNA vaccines in which it is a component.

The following examples are used to further illustrate the importance of the present invention, and are not intended to limit the claims of the invention. Of particular importance is that "E7" as stated in this invention refers to the E7 gene of ANY subtype of Human Pappilomavirus.

EXAMPLES

DNA Constructs and Preparation

IL-6 was amplified by polymerase chain reaction (PCR) using human placenta complementary DNA as the template and a set of primers, namely, 5'-CCGCTCGAGAGGAGC-CCAGCTATGAACTC-3' (SEQ ID NO: 1) and 5'-CCG-GAATTCGACCAGAAGAAGGAATGCCC-3' (SEQ ID NO: 2). The amplified IL-6 nucleotide sequence (SEQ ID NO: 3) was then cloned into the XhoI/EcoRI sites of pcDNA3 vector (Invitrogen, Carlsbad, Calif.) to generate pcDNA3-IL-6.

Figure 1:
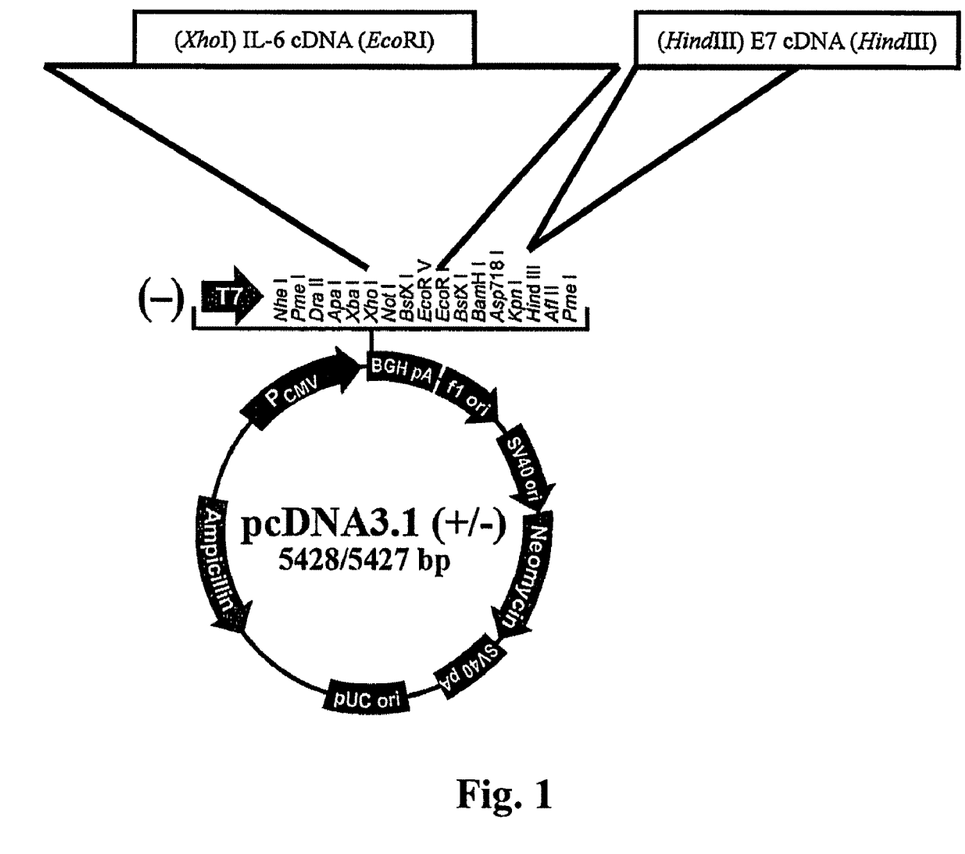
FIG. 1 is the schematic diagram of the DNA construct pcDNA3-IL-6/E7.

E7 was amplified by PCR using the DNA of the CaSki cell line (a cell line containing an integrated HPV 16 genome, obtained from ATCC) as the template and with a set of primers, 5'-CCGGAAGCTTATGCATGGAGATACACCTAC-3' (SEQ ID NO: 4) and 5'-CCCAAGCTTTTGAGAACA-GATGG-3' (SEQ ID NO: 5). The amplified E7 nucleotide sequence (SEQ ID NO: 6) was then cloned into the Hindil sites of pcDNA3 and pcDNA3-IL-6 to generate pcDNA3-E7 and pcDNA3- IL-6/E7 (see FIG. 1) respectively. Said pcDNA3-IL-6/E7 contains the IL-6 and E7 nucleotide sequences joined in a continuous open reading frame such that a fusion protein comprised of IL-6 and E7 are expressed by the construct. In addition, the E7 nucleotide sequence was also cloned into the Hindil sites of pcDNA3-Mcl-1 (a gift from Dr. HL Yen-Yang of Academia Sinica, Taiwan) to generate pcDNA3-Mcl-1/E7.

Next, pcDNA3-IL-6/E7 or pcDNA3-Mcl-1/E7 was digested by HindIII, and then the GFP fragment obtained from the plasmid pcDNA3-E7/GFP (a gift from Dr. T C Wu of Johns Hopkins Medical Institutes) by EcoRI/NotI digestion filled and ligated to generate pcDNA3-IL-6/E7/GFP and pcDNA3-Mcl-1/E7/GFP. All DNA constructs were confirmed by DNA sequencing.

Mice

Six- to eight-week-old female C57BL/6J mice were used in groups of five in all of the subsequently described studies. All animal procedures were performed according to approved protocols and in accordance with recommendations for the proper use and care of laboratory animals at the animal care facility of the College of Medicine, National Taiwan University.

DNA Vaccination

Preparation of DNA-coated gold particles and particle-mediated DNA vaccination using a helium-driven gene gun were performed by a low pressure-accelerated gene gun (Bio-Ware Technologies Co. Ltd., Taipei, Taiwan). The gold particles (Bio-Rad 1652263) were weighted and suspended in 70% ethanol. This suspension was vortexed vigorously and then centrifuged to collect the particles. After washing with distilled water three times, 0.025 µg of the collected gold particles were put in an Eppendorf tube and mixed with 100 µL of 0.05 M spermidine by vortexing, and the mixture was sonicated for 10 to 20 seconds. Subsequently, 25 µg of DNA dissolved in 25 µL of ddH$_2$O was added and the mixture was vortexed. 100 µL of 1 M CaCl$_2$ was added, and the final mixture was vortexed and incubated on ice for 10 minutes to coat DNA on the gold particles via spermidine. Finally, the coated particles were washed with 100% ethanol three times and resuspended in 200 to 250 µL of 100% ethanol. The DNA-coated gold particle suspension was used as a bullet for the gene gun. Naked DNA dissolved in ddH$_2$O or PBS also can be used as a bullet. DNA-coated gold particles were delivered to the shaved abdominal region of mice using the low pressure-accelerated gene gun with a 50 psi discharge pressure of helium.

Intracellular Cytokine Staining and Flow Cytometric Analysis

Each group of mice was immunized with one of the following DNA vaccines: pcDNA3 (no insert), pcDNA3-E7, pcDNA3-IL-6, pcDNA3-E7$^{+pcDNA}$3-IL-6, pcDNA3-Mcl-1/E7 and pcDNA3-IL-6/E7 (2 mg DNA construct/2 mg gold particle/mouse); all mice received a booster immunization one week later. A DNA-naïve group, in which the mice were not vaccinated, was used as a negative control. One week after boosting, the mice were sacrificed and their splenocytes were harvested and incubated with either 1 mg/ml of short E7 peptide RAHYNIVTF (aa 49-57, SEQ ID NO: 7) or 10 mg/ml of long E7 peptide DSSEEEDEIDGPAGQAEPDRA HYNIVTFCCKCDSTLRL (aa 30-67, SEQ ID NO: 8). Generally speaking, the short E7 peptide could be presented directly; however, the long E7 peptide required up-take by the APCs first for subsequent processing and presentation. The cells were mixed with the short or long E7 peptide for 16 to 20 hours. Next, 1 mL/mL Golgistop (PharMigen, San Diego, Calif.) was added to prevent the secretion of cytokines, such as IFN-g or IL-4. Six hours later, cells were harvested, transferred into a tube, and then centrifuged at 1,200-1,600 rpm for 5 min at 4° C. Next, the cells were washed with 500 mL FACScan buffer (0.5% BSA in PBS), and re-centrifuged for 5 min at 4° C. The cells were re-suspended in 1 mL (0.5 ug) PE-conjugated anti-CD4 or anti-CD8 Ab (PharMingen) diluted in 50 mL FACScan buffer, and the cells, were incubated for 30 minutes in the dark. The cells were then washed twice with FACScan buffer and centrifuged. These cells were re-suspended in 500 mL fixation buffer on ice for 20 minutes in the dark; subsequently, the cells were again centrifuged and washed with 500 mL Perm Wash buffer (BioLegend Biotech). 1 mL (0.5 ug) FITC-conjugated anti-IFN-g Ab (PharMingen) or anti-IL-4 Ab (Biolegend, San Diego, Calif.) was diluted in 50 mL Perm Wash buffer, added to the cells, and incubated on ice for 30 minutes in the dark. The cells were centrifuged and washed twice with 500 mL Perm Wash buffer. Then the cells were resuspended in 300 to 500 mL FACScan buffer, and analyzed by flow cytometry. All double-stained cells are analyzed by FACScan or FACSCalibur with CELLQuest software (Becton Dickinson Immunocytometry System, Mountain View, Calif., USA) using a standard procedure. The results are shown in FIG. 2.

Figure 2:
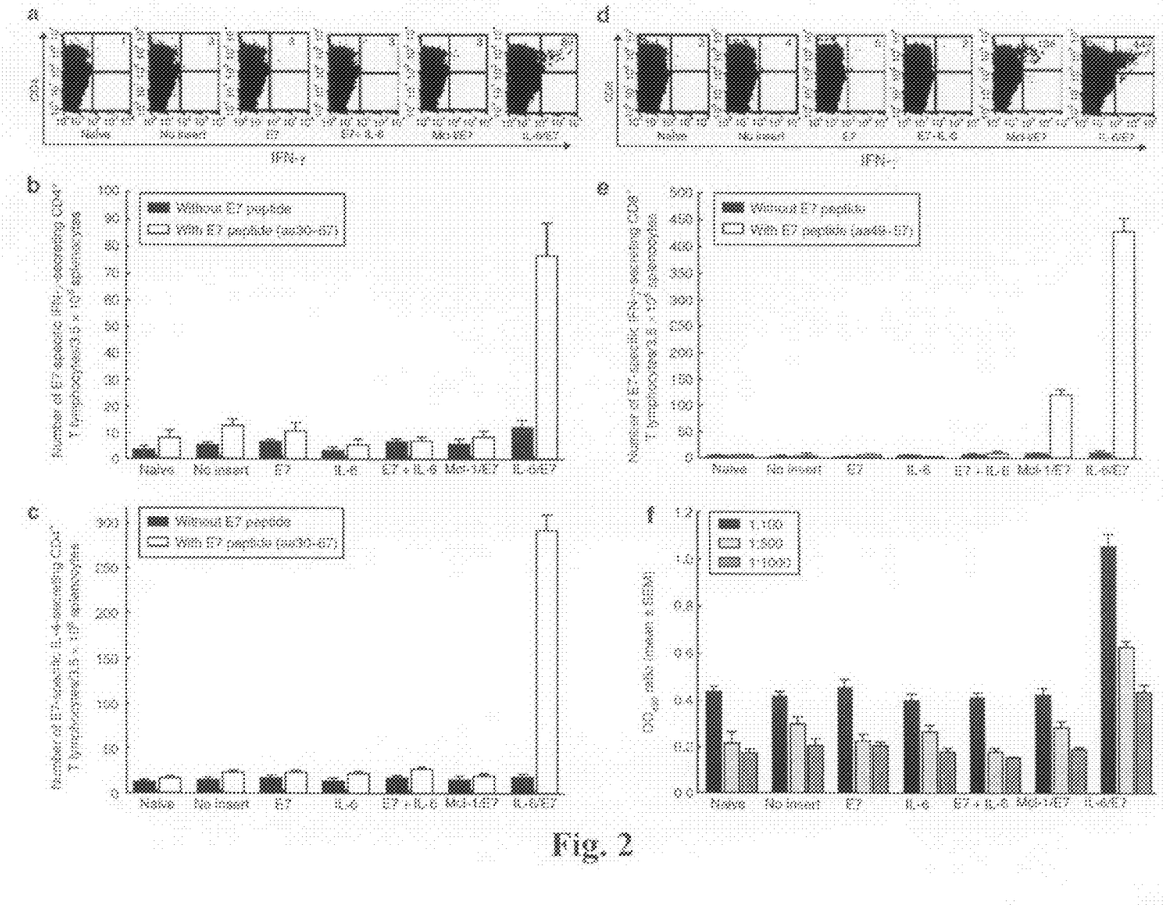

FIG. 2a shows the flow cytometric analysis of E7-specific IFN-g-secreting CD4$^+$ T lymphocytes, and Figs. 2b and 2c are the bar graphs depicting the number of E7-specific IFN-g-secreting CD4$^+$ T lymphocytes and E7-specific IL-4-secreting CD4$^+$ T lymphocytes per 3.5'10$^5$ splenocytes, respectively. These data show that the group of mice vaccinated with IL-6/E7 generated more E7-specific IFN-g-secreting CD4$^+$ T lymphocytes and E7-specific IL-4-secreting CD4$^+$ T lymphocytes than other groups. In other words, IL-6/E7 could activate Th1 pathway (FIG. 2b) and Th2 pathway (FIG. 2c).

FIG. 2d shows the flow cytometric analysis of E7-specific IFN-g-secreting CD8$^+$ T lymphocytes, and FIG. 2e is a bar graph depicting the number of E7-specific IFN-g-secreting CD8$^+$ T lymphocytes: IL-6/E7 activated cytotoxic T lymphocytes (FIG. 2e).

Regardless which E7 peptide was used in these experiments, the numbers of CD4$^+$ IFN-γ-secreting and CD8$^+$ IFN-γ-secreting E7-specific T lymphocytes was significantly higher in the IL6/E7 vaccinated mice as compared to those vaccinated with E7 alone.

Enzyme-Linked Immunosorbent Assay (ELISA) for Anti-E7 Antibodies

Sera from all mice were extracted 14 days after the last immunization and were used to detect HPV-16 E7-specific antibodies by the direct enzyme-linked immunosorbent assay described below.

A 96-microwell plate was coated with 100 μL of bacteria-derived HPV-16 E7 protein (0.5 μg/ml) and incubated at 4° C. overnight. The wells were then blocked with PBS containing 20% fetal bovine serum at 37° C. for 2 hours. 100 μL of the sera at various dilutions of 1:100, 1:500, or 1:1,000 in PBS was then added and the plate was incubated at 37° C. for 2 hours. The wells were then washed with PBS containing 0.05% Tween 20, and then incubated with a 1:2000 dilution of peroxidase-conjugated rabbit anti-mouse IgG antibody (Zymed, San Francisco, Calif.) at room temperature for 1 hour. The plate was washed, developed with 1-Step Turbo TMB-ELISA (Pierce, Rockford, Ill.), and the reaction was stopped with 1M $H_2SO_4$. The ELISA plate was read with a standard ELISA reader at 450 nm.

FIG. 2f shows E7-specific antibodies in mice vaccinated with the various DNA vaccines. Mice vaccinated with the IL-6/E7 DNA vaccine had a titer higher than those in the other groups.

In Vivo Tumor Protection Experiments

To determine whether the observed enhancement of E7-specific T cell immunity can be translated into a significant E7-specific protective anti-tumor effect, we performed the following in vivo tumor protection experiments. Each group of mice was immunized with pcDNA3 (no insert), pcDNA3-E7, pcDNA3-IL-6, pcDNA3-E7+pcDNA3-IL-6, pcDNA3-Mcl-1/E7 or pcDNA3-IL-6/E7 (2 μg/mouse), and all mice received a booster one week later. Mice were challenged with $5 \times 10^4$ TC-1 cells/mouse by subcutaneous injection one week after the boosting. These mice were monitored until 60 days after TC-1 challenge. The naïve group, in which the mice were not vaccinated, was used as a negative control.

TC-1 cells were grown in RPMI-1640 supplemented with 10% (vol/vol) fetal bovine serum, 50 units/mL penicillin/streptomycin, 2 mM L-glutamine, 1 mM sodium pyruvate, 2 mM non-essential amino acids (Gibco company) and 0.4 mg/mL G418 at 37° C. with 5% $CO_2$. On the day of tumor challenge, TC-1 cells were harvested by trypsinization, washed twice with 1× PBS and finally re-suspended in 1× Hanks buffered salt solution for TC-1 challenge.

Figure 3:
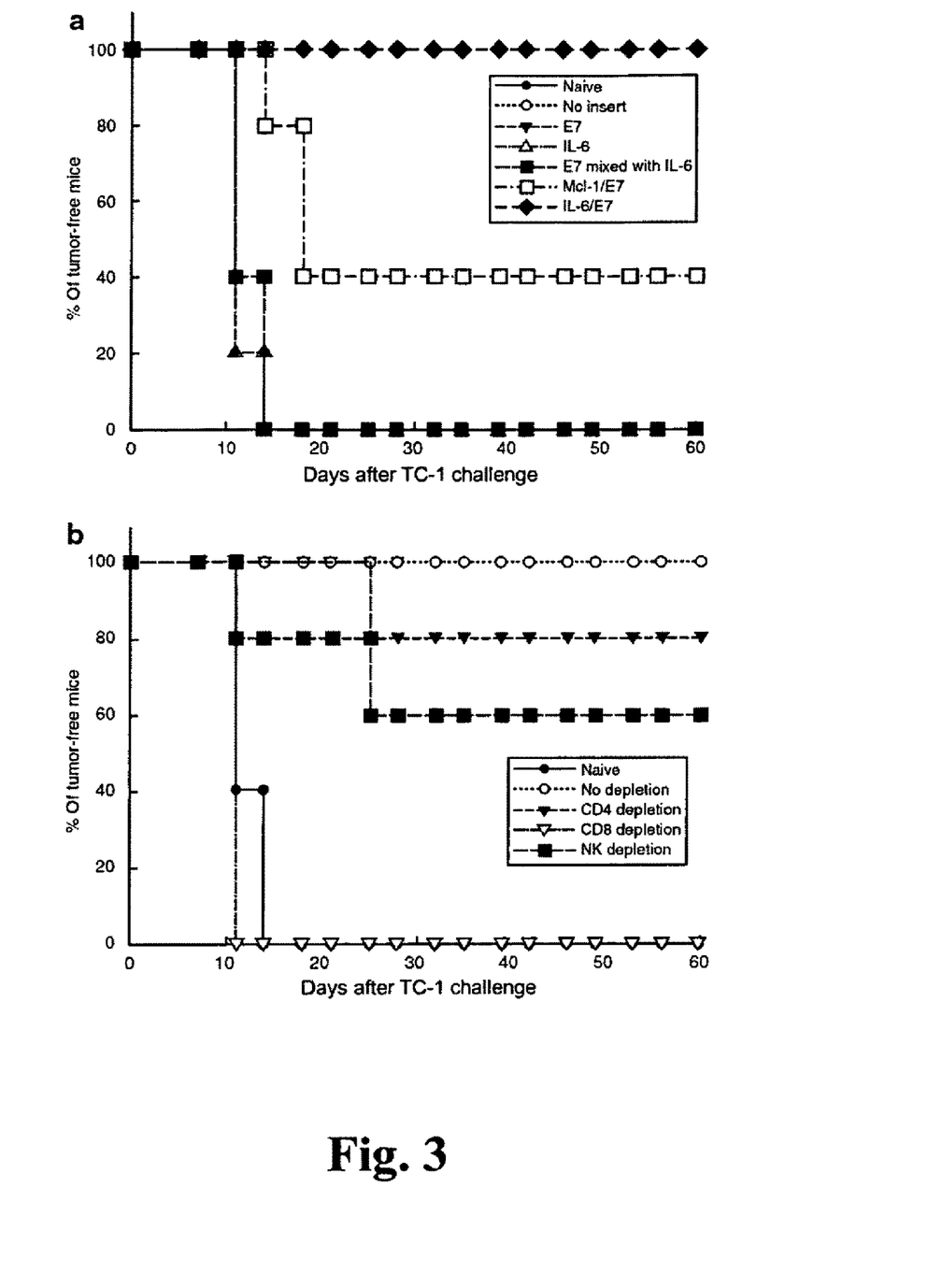
FIG. 3 shows the results of in vivo tumor protection experiments and in vivo antibody depletion experiments in mice. (a) In vivo tumor protection experiments in mice vaccinated with various DNA vaccines. (b) In vivo antibody depletion experiments in mice vaccinated with the IL-6/E7 DNA vaccine.

After challenging with TC-1 tumor cells, 100% of the mice that received the IL-6/E7 DNA vaccine remained tumor-free at day 60. Only 40% of the mice that received the Mcl-1/E7 DNA vaccine remained tumor-free at day 60, and all mice in the other groups, including the E7 group, developed tumors within 14 days after TC-1 challenge. The results are shown in FIG. 3a.

In Vivo Antibody Depletion Experiment

To determine whether the subsets of lymphocytes ($CD4^+$ T lymphocytes, $CD8^+$ T lymphocytes and NK lymphocytes) are important for the anti-tumor effects, we performed an in vivo antibody depletion experiment. The mice were vaccinated with IL-6/E7 DNA vaccine, boosted one week later, and then subjected to lymphocyte subset depletion. Monoclonal Ab GK1.5 was used for CD4 depletion (Berkeley Antibody Company), monoclonal Ab 2.43 for CD8 depletion (Berkeley Antibody Company), and monoclonal Ab PK136 for Natural Killer $1.1^+$ depletion (Berkeley Antibody Company).

The monoclonal antibodies were injected intraperitoneally. One week after depletion, all groups of mice were challenged with $5 \times 10^4$ TC-1 cells/mouse. Flow cytometric analysis revealed that 99% of these lymphocyte subsets were depleted while the other subsets were maintained at normal levels (data not shown). All mice were terminated on day 40 after the tumor challenge.

All naïve mice and all mice depleted of $CD8^+$ T cells grew tumors within 14 days after TC-1 challenge. In addition, 20% of mice depleted of $CD4^+$ T cells and 40% of mice depleted of natural killer $1.1^+$ cells developed tumors within 60 days after TC-1 challenge. The results are shown in FIG. 3b, which suggests that $CD8^+$ T cells, $CD4^+$ T cells, and NK cells are all important for the anti-tumor immunity generated by the IL-6/E7 DNA vaccine.

In Vivo Tumor Treatment Experiment

The therapeutic potential of the chimeric IL-6/E7 DNA vaccine was assessed by a lung hematogenous spread model because of its similarity to cancer metastasis (see Cheng et al., 2005a). In this experiment, mice were injected with $5 \times 10^4$ TC-1 cells via their tail veins. Two days later, each group of mice was immunized with pcDNA3 (no insert), pcDNA3-E7, pcDNA3-IL-6, pcDNA3-E7+pcDNA3-IL-6, pcDNA3-Mcl-1/E7 or pcDNA3-IL-6/E7 (16 μg/mouse), followed by a booster immunization every 7 days. The mice were sacrificed and their lungs were removed 28 days after TC-1 challenge. The pulmonary tumor nodules in each mouse were evaluated and counted by experimenters who were blind to the sample identity. The naïve group, in which the mice were not vaccinated, was used as a negative control.

Figure 4:
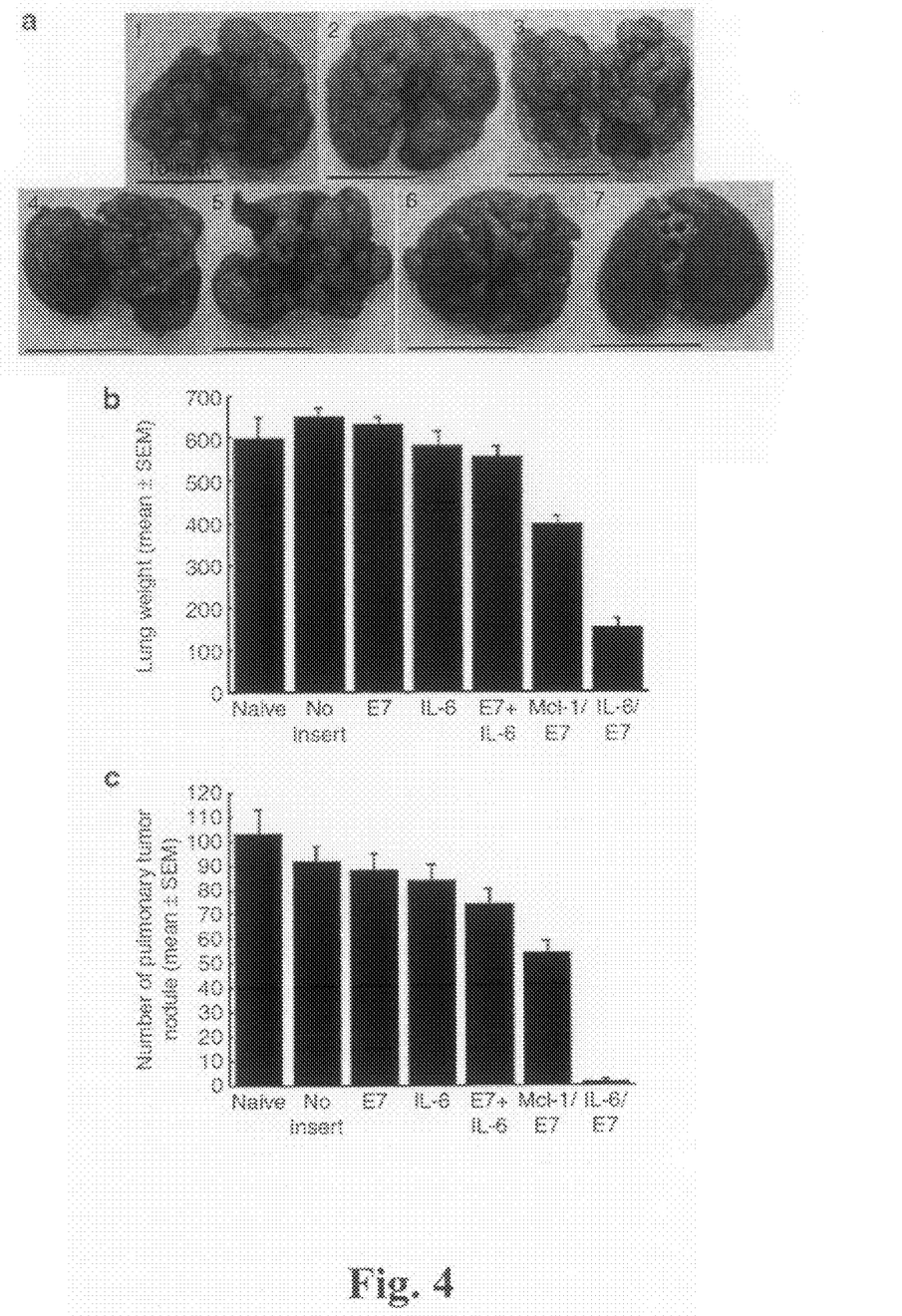
FIG. 4 shows the results of in vivo tumor treatment in mice using a high therapeutic dose. (a) Representative pulmonary tumor nodules of each vaccinated group. 1: naïve, 2: no insert, 3, E7, 4: IL-6, 5, E7+IL-6, 6: Mcl-1/E7, 7: IL-6/E7. (b) The lung weight of each vaccinated group (mean±SEM, P<0.001, one-way ANOVA). (c) The number of pulmonary tumor nodules of each vaccinated group (mean±SEM, P<0.05, one-way ANOVA).

The representative pulmonary tumor nodules of each vaccinated mice group are shown in FIG. 4a, and the mean of lung weight and the number of pulmonary tumor nodules of each vaccinated mice group are shown in FIGS. 4b and 4c, respectively. Mice vaccinated with IL-6/E7 had much lower lung weights in comparison to mice in the other groups, and they also had significantly fewer pulmonary tumor nodules than all the other groups.

Figure 5:
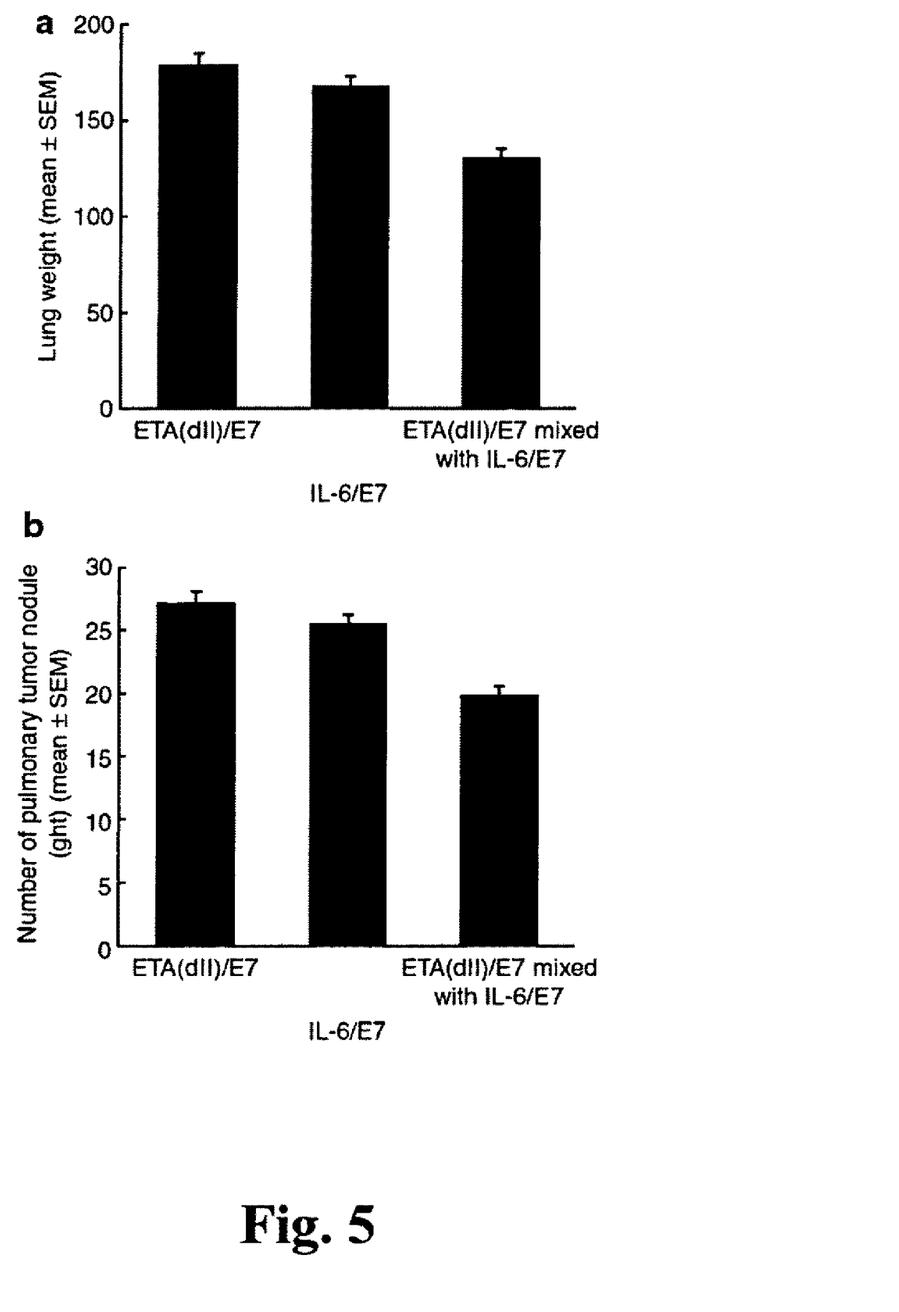
FIG. 5 shows the results of in vivo tumor treatment experiments comparing the anti-tumor effect in mice treated with different chimeric DNA vaccines. (a) the lung weight of each vaccinated group (mean±SEM, P<0.001, one-way ANOVA). (b) the number of pulmonary tumor nodules in each vaccinated group (mean±SEM).

For a direct comparison of chimeric DNA vaccines, mice were grouped and immunized using three different vaccine combinations: IL-6/E7 DNA only, ETA(dII)/E7 DNA only (Hung et al., 2001), or IL-6/E7 mixed with ETA(dII)/E7 DNA, and followed by a booster every 7 days. These mice were killed 28 days after TC-1 challenge to evaluate pulmonary tumor nodules as described above. The results are shown in Figs. 5a and 5b. Among the three groups of mice, mice vaccinated with IL-6/E7 mixed with ETA(dII)/E7 have the lowest lung weight and fewest pulmonary tumor nodules. The results are shown in FIG. 5.

Preparation of $CD11c^+$ Dendritic Cells in the Inguinal Lymph Nodes from Vaccinated Mice Mice received an intradermal injection of pcDNA3-GFP, pcDNA3-E7/GFP, pcDNA3-Mcl-1/E7/GFP or pcDNA3-IL-6/E7/GFP by a gene gun in the abdominal region. Inguinal lymph nodes of all mice were harvested 1 day or 5 days after vaccination. Dendritic cells, which express $CD11c^+$ on the cell surface, were enriched from lymph nodes by CD11c (N418) microbeads (Miltenyi Biotec, Auburn, Calif.). Detection of apoptotic cells in the $GFP^+$ $CD11c^+$ cells was performed using the annexin V-PE apoptosis detection Kit-I (BD Bioscience, San Diego, Calif.) to count the percentage of apoptotic cells by flow cytometry. The naïve group, in which the mice were not vaccinated, was used as a negative control. In addition, $2 \times 10^4$ above-mentioned enriched $CD11c^+$ dendritic cells were incubated with $2 \times 10^6$ E7-specific $CD8^+$ T cell line (see Kim et al., 2003). These cells were then stained for both surface CD8 and intracellular IFN-γ, and then analyzed by flow cytometry as described.

Figure 6:
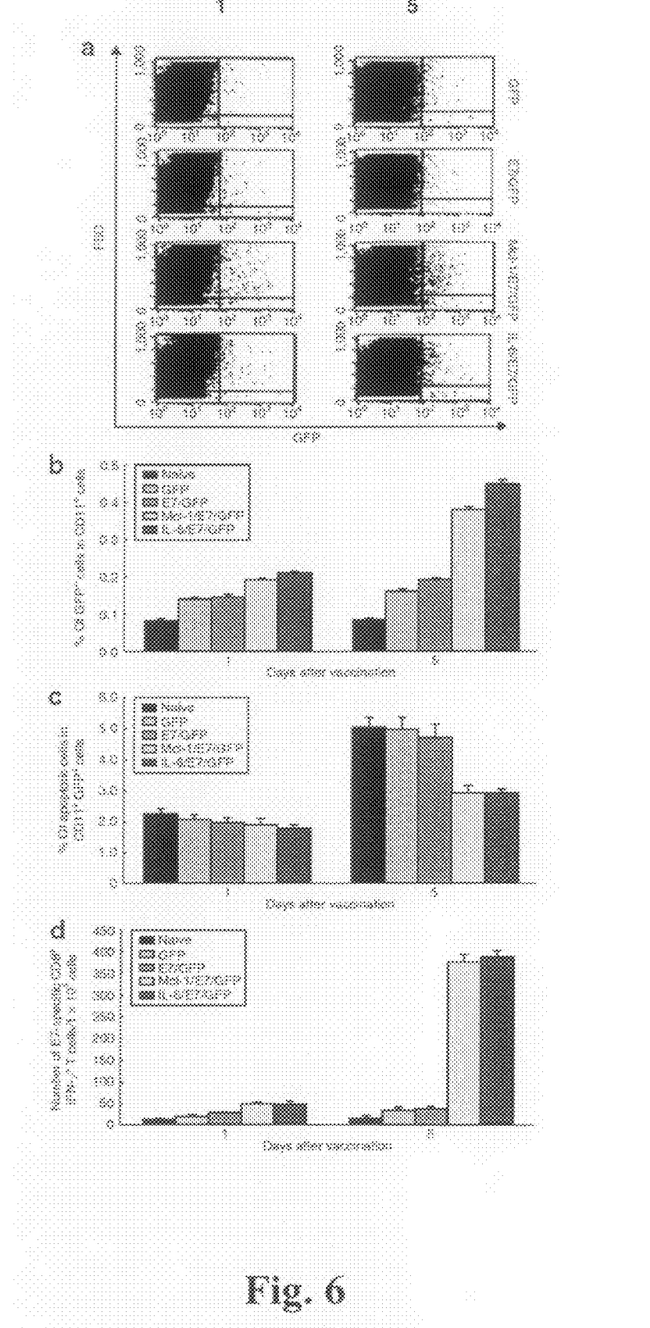
FIG. 6 shows flow cytometric analysis of DNA-transfected dendritic cells in the inguinal lymph nodes of vaccinated mice and activation of E7-specific CD8$^+$ T cells isolated from the inguinal lymph nodes of vaccinated mice. (a) Representative flow cytometry data for the percentage of GFP-transfected CD11c$^+$ cells among the gated monocytes. (b) Bar graph depicting the percentage of CD11c$^+$ GFP$^+$ monocytes among the gated monocytes (mean±SEM, P<0.01, one-way ANOVA). (c) Bar graph depicting the percentage of apoptotic cells in CD11c$^+$ GFP$^+$ cells (mean±SEM, P<0.01, one-way ANOVA). (d) Bar graph depicting the percentage of E7-specific IFN-γ-secreting CD8$^+$ T cell per $1 \times 10^5$ cells (mean±SEM, P<0.001, one-way ANOVA).

Results of the flow cytometric analysis are shown in FIG. 6a, and the results of from the apoptosis detection kit are shown in FIGS. 6b-6d. As shown in FIG. 6b, there was no significant difference in the numbers of GFP⁺ CD11c⁺ cells in the inguinal lymph nodes at day 1 after vaccination. At day 5, however, we found a greater percentage of GFP⁺ CD11 c⁺ cells in lymph nodes harvested from mice vaccinated with Mcl-1/E7/GFP and IL-6/E7/GFP than that of the groups E7/GFP and GFP only.

We further assayed the apoptotic cells in GFP⁺ CD11c⁺ cells derived form the inguinal lymph nodes of these groups. Mice vaccinated with DNA encoding IL-6/E7/GFP or Mcl-1/E7/GFP had a significantly lower percentage of apoptotic cells than mice vaccinated with GFP or E7/GFP, as shown in FIG. 6c. In other words, the apoptosis of dendritic cells is inhibited by IL-6/E7 or Mcl-1/E7 DNA vaccination.

The ability of the enriched CD11c⁺ dendritic cells to stimulate IFN-γ secretion was also evaluated. As shown in FIG. 6d, we compared the enriched CD11c⁺ dendritic cells 1 day and 5 days after gene gun vaccination. The CD11c⁺ dendritic cells isolated from the mice vaccinated with IL-6/E7/GFP or Mcl-1/E7/GFP were more effective in activating the E7-specific CD8⁺ T cell line to secrete IFN-γ than those isolated from the mice vaccinated with GFP and E7/GFP.

Cytotoxic T-Lymphocyte (CTL) Assays Using CaSki Cells as Target Cells

Peripheral blood mononuclear cells were obtained from HLA-A2-positive human volunteers and were induced to differentiate into dendritic cells (DCs) by exposure to granulocyte macrophage colony-stimulating factor (GM-CSF) (800 U/ml) and IL-4 (500 U/ml) for 6 days. The differentiated DCs were grouped and each group was pulsed with 50 mmol/l of cell lysates obtained from 293 $D^bK^b$ cells transfected with pcDNA3 (no insert), pcDNA3-E7, pcDNA3-IL-6 or pcDNA3-IL-6/E7 DNA constructs overnight, and each group of pulsed DCs was then incubated with fresh peripheral blood mononuclear cells from the same human volunteers to generate four sets of E7-specific CD8⁺ T cells. CTL assays were then performed wherein each E7-specific CD8⁺ T cell sets were used as effector cells and CaSki cells were used as the target cells. The cytotoxic T cell activity (CTL) level was measured using a standard lactate dehydrogenase (LDH) release assay (see Cheng et al., 2005b). Effector cells and target cells ($1 \times 10^4$ target cells per well) were mixed together at a variety of ratios (1:1, 5:1, 15:1 and 45:1) in a final volume of 200 μL. The cell mixtures were incubated for 5 hours at 37° C., and then 50 μL of the culture medium was collected to assess the quantity of LDH in the culture medium and count the percentage of cell lysis according to the protocol of the CytoTox assay kits (Promega, Madison, Wis.). All experiments were performed in triplicate.

Figure 7:
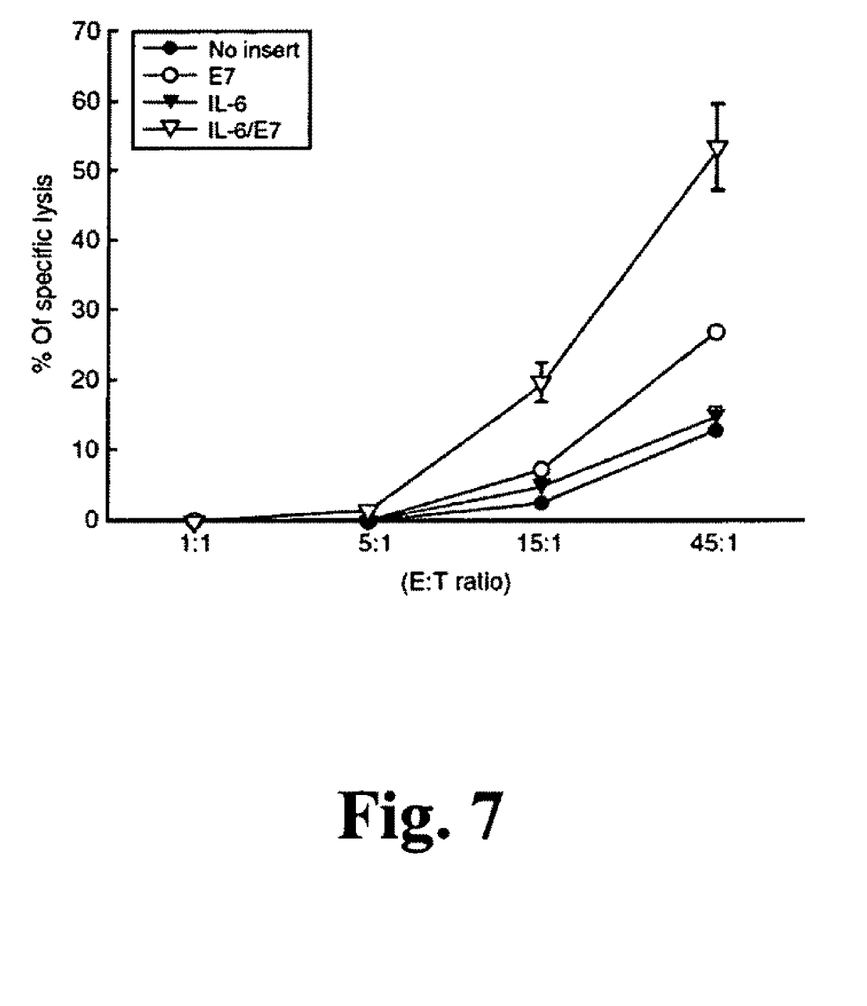
FIG. 7 shows CTL assay results of E7, IL-6 and IL-6/E7, in which E7, IL-6 or IL-6/E7 protein-pulsed E7-specific CD8$^+$ T cells used as effectors with CaSki cells used as targets. E:T ratio, effector-to-target ratio; IL-6, interleukin-6.

As shown in FIG. 7, the percentage of specific lysis of CaSki cells obtained from IL-6/E7 protein-pulsed cytotoxic T cells was significantly higher than that obtained from E7 protein-pulsed E7-specific cytotoxic T cells.

Statistical Analysis

All data expressed as mean±SEM are representative of at least two different experiments. Data for intracellular cytokine staining with flow cytometric analysis and tumor treatment experiments were evaluated by analysis of variance (ANOVA).

What is claimed is:

1. A DNA construct, consisting of:
   an expression vector, which is expressible in a eukaryotic cell;
   an Interleukin-6 (IL-6)-encoding sequence; and
   a Human papillomavirus E7 (HPV E7)-encoding sequence;
   wherein the IL-6-encoding sequence consists of SEQ ID NO: 3, and HPV E7-encoding sequence consists of SEQ ID NO: 6.

2. The DNA construct according to claim 1, wherein said expression vector is expressible in human cells.

3. The DNA construct according to claim 2, wherein said expression vector is selected from pcDNA3, pSG5, or pCMV.

4. The DNA construct according to claim 3, wherein said expression vector is pcDNA3.

5. A DNA vaccine, comprising:
   the DNA construct according to claim 1; and
   a particle, which is coated with said DNA construct.

6. The DNA vaccine according to claim 5, wherein said particle is a gold particle.

7. The DNA vaccine according to claim 6, said gold particle has a diameter of 1.6 μm.

8. The DNA vaccine according to claim 5, wherein said expression vector is expressible in human cells.

9. The DNA vaccine according to claim 8, wherein said expression vector is selected from pcDNA3, pSG5, or pCMV.

10. The DNA vaccine according to claim 9, wherein said expression vector is pcDNA3.

11. The pharmaceutical composition according to claim 5, further comprising a pharmaceutically acceptable carrier.

12. A method of generating the DNA vaccine of claim 5, comprising:
   (1) providing a DNA construct consisting of:
      an expression vector, which is expressible in a eukaryotic cell;
      a nucleotide fragment an Interleukin-6 (IL-6)-encoding sequence; and
      a Human papillomavirus E7 (HPV E7)-encoding sequence;
      wherein the IL-6-encoding sequence consists of SEQ ID NO: 3, and the HPV E7-encoding sequence consists of SEQ ID NO: 6; and
   (2) coating said DNA construct on the surface of a particle.

13. The method according to claim 12, wherein said expression vector is pcDNA3.

14. The method according to claim 12, wherein said particle is a gold particle.

15. The method according to claim 14, said gold particle has a diameter of 1.6 μm.

16. A method for preventing or treating a HPV-induced disease, comprising administering an effective amount of the DNA vaccine according to claim 5 to a subject having or at risk for developing said HPV-induced disease.

17. The method according to claim 16, wherein said HPV-induced disease is cervical cancer, vaginal cancer, vulvar cancer, or penile cancer.

18. The method according to claim 17, wherein said HPV-induced disease is cervical cancer.

19. The method according to claim 16, wherein said HPV-induced disease is a cervical, vulvar, or vaginal precancerous lesion.

* * * * *